United States Patent [19]

Stang et al.

[11] Patent Number: 5,795,586

[45] Date of Patent: Aug. 18, 1998

[54] TOXIN DECONTAMINANT FOOD PRODUCT AND METHOD OF FORMING SAME

[75] Inventors: Michael A. Stang, Pikesville, Md.; Jeffrey Alan Zeak; Brian Lee Strouts, both of Manhattan, Kans.

[73] Assignee: De Novo, Inc., Baltimore, Md.

[21] Appl. No.: 692,239

[22] Filed: Aug. 7, 1996

[51] Int. Cl.⁶ .................................................. A61K 9/28
[52] U.S. Cl. ................. 424/441; 424/125; 504/103; 502/180; 502/416; 514/823; 514/974
[58] Field of Search ...................... 424/125, 441; 504/103; 502/180, 416; 514/823, 974

[56] References Cited

U.S. PATENT DOCUMENTS

| | | |
|---|---|---|
| 294,687 | 3/1884 | Seibert . |
| 1,052,872 | 2/1913 | Williams . |
| 1,542,006 | 6/1925 | Sauer ........................... 424/125 |
| 1,741,589 | 12/1929 | Scott et al. . |
| 2,143,978 | 1/1939 | Rockwell . |
| 2,787,579 | 4/1957 | van der Weel . |
| 3,642,986 | 2/1972 | Welch et al. . |
| 3,917,821 | 11/1975 | Manes . |
| 3,932,661 | 1/1976 | Kaugars ........................ 514/639 |
| 3,934,007 | 1/1976 | Gussin et al. . |
| 4,122,169 | 10/1978 | Geils . |
| 4,162,306 | 7/1979 | Laves . |
| 4,529,583 | 7/1985 | Porter . |
| 4,594,249 | 6/1986 | Procter et al. . |
| 4,761,284 | 8/1988 | Nishimura ..................... 424/125 |
| 4,767,789 | 8/1988 | Blank et al. .................... 514/629 |
| 4,822,765 | 4/1989 | Nishimura . |
| 4,835,186 | 5/1989 | Reuter et al. .................. 514/570 |
| 4,859,476 | 8/1989 | Herting ........................ 426/87 |
| 4,895,723 | 1/1990 | Amer et al. .................... 424/78.12 |
| 5,482,707 | 1/1996 | Saulson ........................ 424/125 |

OTHER PUBLICATIONS

Cheng, M. et al. Vet. Hum. Toxicol., 31(4), p. 332, Aug. 1989.

Boehm, J.J., et al, Aust. J. Pharm. Sci. 7(4), pp. 119–121, Dec. 1978.

Cooney, D.O. et al, Am. J. Hosp. Pharm. 34, pp. 1342–1344, Dec. 1977.

*Primary Examiner*—C. Warren Ivy
*Assistant Examiner*—Garth Dahlen
*Attorney, Agent, or Firm*—Morton J. Rosenberg; David I. Klein; Jun Y. Lee

[57] ABSTRACT

An antidotal food product containing activated charcoal is provided for ingestion into the gastro-intestinal tract of a user. The antidotal food product is orally administered having the visual appearance and physical properties which enables the desire on the part of young children to chew and ingest the food product. The food product in a preferred embodiment includes a substantially dry friable wafer which is adapted to be chewed by the user for ingestion. The dry friable wafer has a wafer mixture composition formed by blending a first predetermined weight of sorbent particulate composition having an initial adsorption value with respect to a toxin to a second predetermined weight of a substantially non-interfering flavored binding composition which provides for a creamy and sweet tasting food product. The initial adsorption value of the sorbent particulate composition maintains a high adsorption value in the wafer mixture composition for maximizing the adsorption value of the composition to combat toxins which have been ingested by the user.

38 Claims, 3 Drawing Sheets

TOXIN DECONTAMINANT FOOD PRODUCT AND METHOD OF FORMING SAME

BACKGROUND OF THE INVENTION

FIELD OF THE INVENTION

The subject antidotal food product containing activated charcoal is generally directed to an antidotal substance to be administered to poisoning victims for decontamination of various poisonous substances that they may have ingested. More specifically, the antidotal food product containing activated charcoal is an orally administered antidotal substance having the visual appearance and physical properties to enable proper oral administration to even young children.

Poisonings by the ingestion of toxic substances have historically been and continue to be a significant problem today. With the ongoing proliferation of an expansive variety of commercially-available household products, access to a plethora of toxic substances just in the average home is currently at or near an all time high. While efforts in recent years, such as conspicuous labelling, tamper-proof sealing campaigns, and limiting the number of tablets in bottles of children's medicines as well as a concerted informational program appear to have been successful in preventing dramatic growths in the number of poisoning incidents that occur annually, significant numbers of poisoning incidents continue to occur, an overwhelming percentage of those incidents occurring at a residence, and the majority of the victims being young children. In 1993 alone, for instance, there were 1,751,476 human poisoning cases reported to recognized poison centers, over 90% of which occurred at a residence, according to the 1993 *Annual Report of the American Association of Poison Control Centers Toxic Exposure Surveillance System*. Children under the age of six made up approximately 56% of the victims in these cases. Considering that only about 70% of the American population actually had access at the time to a poison center recognized in the study, the number of incidents that actually occurred in 1993 is likely to have been significantly higher than these numbers would indicate, with the total number of cases more realistically having been on the order of 2.5 million.

In the emergency treatment of poisoning victims, the effort centers around two main objectives: general support and stabilization of the victim, and decontamination of the victim. As decontamination and treatment must begin immediately in such toxicologic emergencies, often without the benefit of full and thorough clinical information on the patient, it is particularly important that any drug or therapeutic substance administered to the patient be substantially free of unwanted side effects that may cause unforeseen complications, or even death. For this reason, sorbents which, when introduced into the patient's gastro-intestinal tract, resist decomposition and adsorb the ingested toxins until eventual excretion by the patient have been employed for decontamination. Of those sorbents, activated charcoal has emerged in the field of emergency toxicological treatment as the decontaminant of choice. Its routine use in the treatment of poison victims did not become widespread until the 1980s; however, its administration to poisoning victims has now surpassed the administration of syrup of ipecac as the single most important toxicological treatment measure.

Activated charcoal is a fine, black, powdery substance which is tasteless, odorless, and non-toxic. Activated charcoal is generally formed by oxidation (activation) of combustion residue derived from a controlled combustion process performed on wood, peat, or another organic material. The oxidation and controlled combustion steps combine to yield a substance composed of extremely porous particles which give it extraordinarily high internal surface area, typically ranging between 900 and 2000 $m^2/g$. Due to its extraordinary surface area, activated charcoal exhibits great adsorptivity and, thus, has proven to be quite effective as a decontaminant when introduced in sufficient quantities into the gastro-intestinal tract of a poisoning victim. The highly adsorptive activated carbon particles within the gastro-intestinal tract are capable of adsorbing toxin, not only from the contents of the gastro-intestinal tract but even from the blood stream (by "intestinal dialysis") through the blood vessels which supply the gastro-intestinal tract. These toxins, now bound to the activated charcoal, are excreted in the stool.

Activated charcoal is currently available in several forms to be orally administered to poisoning victims. In the most widely used form, activated charcoal is contained in a liquid suspension such as the commercially-available Actidose Aqua and Charcoaid 2000 suspensions. Activated charcoal is also available extensively in Europe, and to a more limited extent in the United States, simply in its powdered or granulated form for mixture within a drinkable liquid prior to ingestion. In yet another form, activated charcoal is contained in over-the-counter tablets or capsules widely available in Europe for the treatment of gas and upset stomach. Use of these tablets or capsules for decontamination in toxicological treatment, however, is not readily feasible. Even if all active ingredients other than activated charcoal were removed therefrom, the relatively high dosages required in most poisoning incidents would necessitate the ingestion of many such tablets or capsules, a daunting task even for the average adult, let alone for the average young child.

In whatever form activated charcoal is delivered to the gastro-intestinal tract, suspended in a liquid, compressed within a tablet or capsule, or simply in its raw powdery state, the activated charcoal is likely to have significantly beneficial, if not life-saving, effects on the poisoning victim -- that is, if it can be properly delivered in the necessary quantities to the gastro-intestinal tract of that victim. Therein lies the single greatest obstacle to optimal utilization of activated charcoal as a decontaminant in toxological treatment. Each of the currently available forms in which activated charcoal is available for oral ingestion utterly fails to adequately induce or at least encourage proper ingestion of a sufficient dose of the activated charcoal by the victim. Essentially, except in the tablet or capsule form (which presents its own obstacles to ingestion), the antidotal substances are extremely unpalatable and, in fact, quite noxious. Liquid antidotal suspensions containing activated charcoal, for instance, form a black, gritty liquid bearing a striking resemblance to expended engine crankcase oil and lacks the pleasant taste which, theoretically, might cause the ingesting individual to even momentarily forget the unpleasant appearance, texture, and consistency of that which he or she is ingesting.

Whereas to a mature adult poisoning victim, the noxiousness of an activated charcoal-containing antidote may simply represent a trivial, though unpleasant, consequence that must be tolerated to avoid the far greater consequences of his or her serious predicament, it would hardly be such a trivial matter to a young child victim. To that young child or any other victim lacking the mental or emotional capacity to fully appreciate the magnitude of the situation and therefore incapable of seeing beyond the overbearing experience of ingesting the given antidote, the palatability of the antidote, both in appearance and taste, will not only determine how pleasant the ingestion experience is, but will actually determine whether or not that ingestion occurs in the first place. That might, in part, explain why with 1,751,476 reported poisoning incidents in 1993, activated charcoal was administered in that year to only 127,857 victims, despite the fact that the relatively risk-free benefits of activated charcoal and toxological treatment had been widely recognized by emergency care providers since well before 1993. Children, especially very young children, who represent the class of individuals most vulnerable to accidental poisonings and who, in fact, make up the majority of the victims in poisoning incidents, are loathe to ingest activated charcoal in the various forms in which it may currently be presented to them.

This fact is borne out by empirical studies performed on the subject, and by the first hand experiences of seasoned emergency health care professionals. For instance, in a 1987 study, Grbcich, et al., "Administration of Charcoal in the Home," *Vet. Hum. Toxicology*, 29, 458 (1987), the authors studied the cases of six children between the ages of one and five years who were given a liquid suspension containing 1 gm/kg of activated charcoal after they had accidentally ingested a toxic substance in amounts that did not necessitate hospitalized treatment. Of those children, none ingested the full amount of the suspension given to him or her, and only one ingested as much as half of the amount given. The authors observed that "all parents had considerable difficulty getting the child to drink the charcoal [suspension,] and most indicated they would not choose this method of oral decontamination in the event of a future poisoning." The experiences in the emergency room have been, by and large, no different from the experiences of these parents, for most health care providers currently consider themselves extremely fortunate if they are able to coax, trick, or otherwise prompt a young child poisoning victim to ingest any amount of an activated charcoal antidote.

Faced with this obstacle, forced ingestion is not a viable option. Aside from its moral and legal implications, forced ingestion would pose a substantial collateral health risk. The direct health risks of activated charcoal therapy are nominal, if any, but one indirect risk, the serious occurrence of which has been reported in a few cases, is that of activated charcoal aspiration by the victim. While the risk of aspiration accompanies any oral ingestion of a substance, that risk is greatly amplified where ingestion of the substance is imposed upon a non-cooperative child who is instinctively resisting that ingestion. The risk becomes even greater where the ingestion is being forced by the child's parent, guardian, or any other individual having a personal relationship with the child, who might himself or herself understandably be in an excited, agitated, or even bewildered state given the exigencies surrounding a typical poisoning incident.

In cases where activated charcoal must be administered to an uncooperative patient, there is no choice but to introduce it through a nasogastric or orogastric tube. This procedure often requires physically restraining the patient. It also carries the risks of trauma to the mouth, pharynx, esophagus and stomach. Inadvertent placement into the tracheobronchial tree can result not only in trauma to these areas but in massive charcoal aspiration which can be fatal.

Efforts have been made to render the currently available forms of activated charcoal antidotes more palatable, but those efforts have at best yielded only antidotes that may be somewhat less noxious, but certainly not palatable, especially to young children. What is more, those efforts have often led to the introduction into the antidote of components which actually diminish the adsorptivity of the activated charcoal, thereby undermining the singular essential function of the antidote.

What is currently needed, therefore, is an antidotal product containing ample quantities of activated charcoal which is palatable to young children and in which the adsorptivity of the activated charcoal is not diminished in any substantial measure. It is absolutely essential that the antidotal product not only be palatable enough to entice the average young child to place it into his or her mouth, but that the product also be palatable enough to encourage the child to willingly swallow and continue to willingly swallow relatively large quantities thereof.

The antidotal food product containing activated charcoal of the present invention is an antidotal product which uniquely provides the necessary palatability not heretofore seen in prior art antidotes. In its preferred embodiment, the subject antidotal food product is in the form of a readily recognizable cookie sandwich having a pair of black wafers sandwiching a creamy filling. The subject antidotal food product in this form has the appearance, weight, and feel of very common and popular cookie treats. To the average young child, the subject antidotal food product is, thus, indistinguishable from the delectable cookie treats he or she is accustomed to eating.

The subject antidotal food product also incorporates a number of component compositions which give it a pleasant flavor and a texture not unlike that of the commonly-available cookie treats. Thus, a child would not only be enticed to place the subject antidotal food product into his or her mouth, he or she would actually be encouraged thereafter to chew and swallow the product. The pleasant taste would encourage the child to so ingest additional portions of the product if necessitated by the required activated charcoal dosage.

An important factor in the proper use of activated charcoal or any other decontaminant in toxological treatment is, in addition to its ingestion in sufficient doses by the victim, the promptness with which that ingestion occurs. Ideally, the activated charcoal ought to be administered at the site at which the poisoning incident occurs (which in most cases is the victim's home) immediately following the accidental ingestion, before the ingested toxins have had the opportunity to be extensively absorbed into the blood stream. Yet, most likely due to the difficulty of administering them arising from their unpalatability, currently available activated charcoal antidotes are almost exclusively administered in medical institutions, often many precious minutes, if not hours, after the accidental toxic ingestion has occurred. Given its inherent palatability, the subject antidotal food product, in contrast, could easily be administered in the home or any other setting outside a medical institution. Hence, the subject antidotal food product would not only expand the usage of activated charcoal as a decontaminant, it would actually enhance in a significant manner the effectiveness of that usage.

While the subject antidotal food product successfully incorporates with activated charcoal other component compositions which combine therewith to yield heretofore unsurpassed palatability without diminishing the decontaminating function of the activated charcoal; it must be recognized that due to the properties and characteristics of activated charcoal, developing the proper combinations was hardly a trivial task. One cannot simply blend a pleasant tasting composition with activated charcoal to form a useful antidotal product. Many substances will tend in varying degrees to bind with the activated charcoal particles and significantly diminish, even completely nullify, its adsorptivity. An end product would then result which is either devoid of a decontaminating capability, or which requires the ingestion of much too great a quantity to be of any practical use.

Realization of the unique combination of component compositions that essentially form the subject antidotal food product was the result of extensive testing and research. That testing and research is described in great detail in following paragraphs.

SUMMARY OF THE INVENTION

A primary object of the present invention is to provide an antidotal food product for decontaminating a user of a toxin ingested by him or her.

It is another object of the present invention to provide an antidotal food product which exhibits sufficient palatability to entice and encourage ingestion thereof even by young children.

It is another object of the present invention to provide an antidotal food product incorporating a substantial quantity of a sorbent composition for adsorbing toxins contained in and around the gastro-intestinal tract of the user.

It is another object of the present invention to provide an antidotal food product incorporating a substantial quantity of an activated charcoal composition.

It is another object of the present invention to provide an antidotal food product which contains a substantial quantity of an activated charcoal composition, yet exhibits the appearance, texture, and taste substantially similar to that of a cookie treat commonly consumed by children.

It is another object of the present invention to provide an antidotal food product which co-mingles with an activated carbon composition incorporated therein a flavoring composition which does not substantially diminish the adsorptivity of the activated charcoal composition.

It is yet another object of the present invention to provide an antidotal food product having a pair of wafer portions, each incorporating substantial quantities of an activated charcoal composition blended with a flavoring composition, and a flavored, creamy filling portion sandwiched therebetween.

It is another object of the present invention to provide an antidotal food product which may be conveniently stored and safely administered at a site outside a medical institution.

These and other objects are attained by the subject antidotal food product which is adapted for ingestion by a user for decontaminating that user of a toxin ingested by him or her, and which emulates in taste, texture, and appearance a readily identifiable food product. The antidotal food product includes a solid wafer portion having an outer contour substantially equivalent to that of the identifiable food product, the wafer portion being characterized by an outer texture and a friability that is also substantially equivalent to the outer texture and friability that characterize the identifiable food product. The wafer portion includes a sorbent composition having a predetermined adsorptivity for adsorbing the user-ingested toxin. The wafer portion also includes a flavored binding composition blended with the sorbent composition which adds to the antidote a flavor substantially equivalent to that of the identifiable food product. This flavoring composition is such that it mixes with the sorbent composition without substantially abating the sorbent composition's predetermined adsorptivity; thus, without interfering therewith.

In a preferred embodiment, the sorbent composition of the antidotal food product is an activated charcoal composition having an approximate internal surface area of 2,000 $m^2/g$. The flavored binding composition in that preferred embodiment, includes a corn syrup solids component, a compressible sucrose component, a chocolate cream flavor component, a vanilla dry flavor component, and a sweetener component.

At least a pair of wafer portions are included in the preferred embodiment along with a flavored, creamy filling portion sandwiched therebetween to emulate a readily-identifiable cookie treat. The filling portion includes a powdered sugar component, a high fructose corn syrup component, a vanilla flavoring component, and a salt component.

DETAILED DESCRIPTION OF THE PREFERRED EMBODIMENTS

Figure 1:
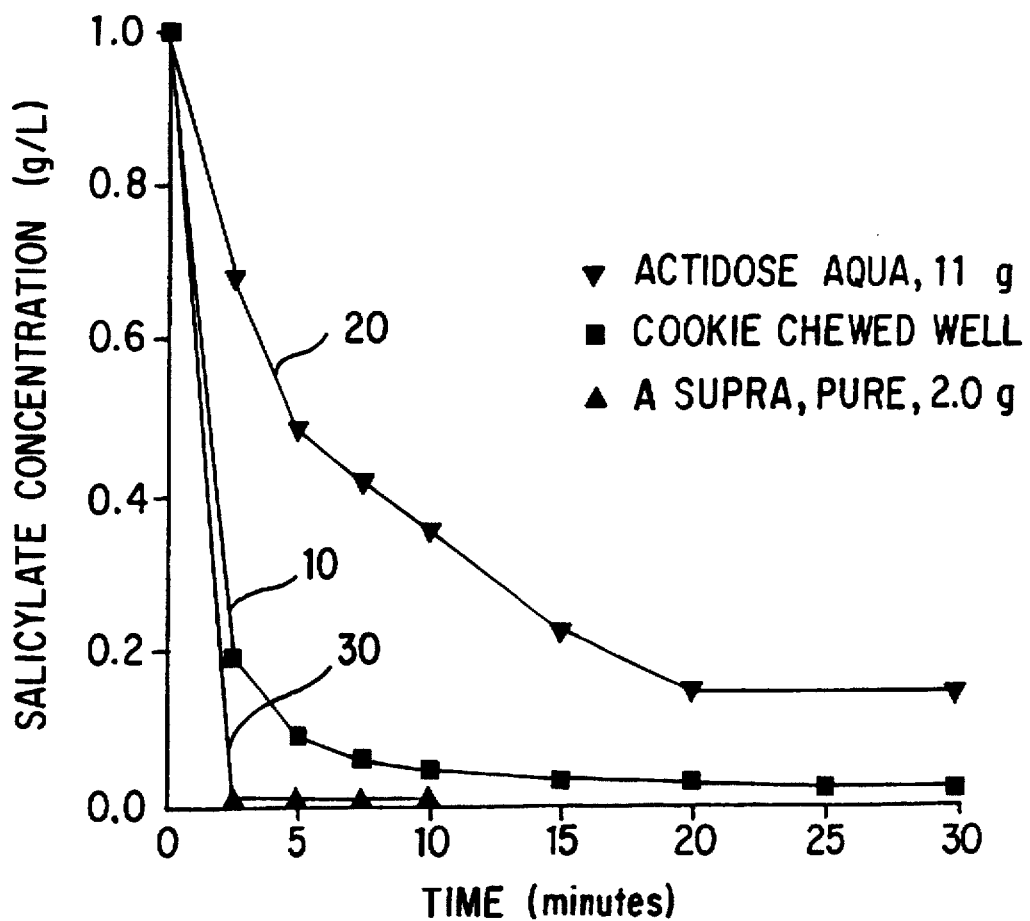
FIG. 1 is a graphical representation of adsorption kinetics test data for the preferred embodiment of the decontaminant food product of the present invention.

In the preferred embodiment, the subject antidotal food product is provided generally in the form of a cookie sandwich treat commonly consumed by and quite popular with young children. It generally exhibits the appearance, the texture, the friability, and the sweet flavor which typically characterize such cookie sandwich treats. Accordingly, one antidotal food product formed in accordance with the overall invention concept as herein described may comprise a pair of biscuit-like wafers and a creamy, preferably white, filling sandwiched therebetween. The wafers may have a coloring resembling popular cookie or wafer like products commercially sold and easily identified by young children to obviously entice them to eat the antidotal food product of the subject invention. Each wafer includes activated charcoal, corn syrup solids, compressible sucrose, chocolate cream flavor, vanilla dry flavor, and sweetener in the approximate weight range proportions indicated in Table 1.

TABLE 1

| COMPOSITION | APPROXIMATE WEIGHT PERCENTAGE RANGE | PREFERRED WEIGHT PERCENTAGE |
|---|---|---|
| Activated Charcoal | 20.0%–60.0% | 40.0% |
| Corn Syrup Solids | 0.0%–78.0% | 28.8% |
| Compressible Sucrose | 0.0%–78.0% | 28.8% |
| Chocolate Cream Flavor | 0.5%–2.0% | 1.0% |
| Vanilla Dry Flavor | 0.5%–2.0% | 1.0% |
| Additive Sweetener | 0.1%–1.0% | 0.3% |

Preferably, a pair of disk-shaped black wafers are formed in accordance with the proportions indicated in Table 1. The wafers exhibit a compressed granular texture and a degree of friability akin to that of a class of cookie treats quite popular with children. The degree of friability is such that the wafers are easily crumbled by the average biting force generated by even a very young child. The degree of friability is also such that the crumbled wafers may thereafter be effectively disintegrated by the subsequent chewing action generated by the given young child.

Subject to the allowable ranges of their component composition weight percentages, the wafers exhibit a degree of rich, sweet flavor to accompany their graham cracker-like crumbly texture. It is important that the sweet flavor of the wafers be sufficient to encourage substantial chewing prior to ingestion into the user's gastro-intestinal tract.

To enhance both the sweet flavor of the wafers, and to enhance the emulation of that readily identifiable class of cookie treats, a creamy white filling is sandwiched between a pair of wafers. The precise consistency, color, and taste of the filling is not important to the invention; however, it is preferable that the filling be of a consistency similar to that found in commonly-consumed cookie sandwich treats, that its color is not one that is non-existent in a commonly consumed cookie sandwich treat, and that its flavor exhibit a sufficient sweet component to supplement or augment the sweet flavor of the wafers. The component compositions and their corresponding proportional weights of one suitable filling composition exhibiting such attributes are indicated in Table 2.

TABLE 2

| COMPOSITION | APPROXIMATE WEIGHT PERCENTAGE RANGE | PREFERRED WEIGHT PERCENTAGE |
|---|---|---|
| Powdered Sugar | 70%–90% | 76.34% |
| High Fructose Corn Syrup | 10%–30% | 22.90% |
| Vanilla Flavor | 0%–2% | 0.63% |
| Salt | 0%–1% | 0.13% |

Turning now to each of the component compositions shown in Table 1 for each wafer, the preferred sorbent composition is activated charcoal, a black, powdery substance characterized by an extraordinary porosity which gives its particles a high internal surface area. A medicinal grade of this activated charcoal is commercially available from a limited number of manufacturers worldwide in forms respectively exhibiting various levels of internal surface area. One line of medicinal grade activated charcoals is manufactured by American Norit Company having designations A Supra, B Supra, and USP XXII, respectively with characteristic surface areas of 2,000, 1,400, and 900 $m^2/g$. Medicinal grade activated charcoal characterized by even greater internal surface areas have been available in the past in the United States but are currently not available commercially. Any medicinal activated charcoal may be used in the subject composition. A Supra was chosen in the preferred embodiment since it represents the largest surface area charcoal currently commercially available in the United States. This may translate into a lesser quantity of charcoal product required.

Lab tests verify that activated charcoal of greater surface area exhibits greater adsorptivity per unit gram thereof. To the extent possible, therefore, it is preferable that activated charcoal of maximum surface area be incorporated into the subject wafer. This would not only tend to decrease the minimum weight percentage necessary in each wafer to enable the incorporation in greater proportional quantities of the other flavor-enhancing compositions, but would also quite simply lessen the dosage that must be ingested for decontamination of a given quantity of ingested toxin.

Referring to the other compositions accompanying activated charcoal in the subject wafer, several factors are of paramount importance in their selection. First, the accompanying compositions must provide for the otherwise tasteless, gritty activated charcoal, a friable, yet chewable texture and a pleasant degree of sweet flavor reminiscent of, if not identical to, a sweet cookie treat. The accompanying compositions must provide such attributes without substantially abating the adsorptivity of the activated charcoal; that is, without interfering therewith. As will be discussed in following paragraphs, that is no trivial matter, as a number of component compositions incorporated into early prototypes of the subject wafer were found to unexpectedly diminish in significant manner the overall adsorptivity of the activated charcoal. The component compositions shown in Table 1, when combined in the proportional quantities indicated, were found to reduce the overall adsorptivity of activated charcoal in its pure form by only approximately 6%. This was determined to be an acceptable tradeoff given the exceptional flavor, texture, and friability level attained in the wafer.

The corn syrup solids composition is a solid form of a corn or glucose syrup which is generally a mixture of D-glucose, maltose, and maltodextrins derived by hydrolysis of corn starch from the action of various acids and enzymes. The composition serves both as a sweetener and a binding agent for binding the activated charcoal particles together in a compressed solid. The particular type of corn syrup solids composition is not important to the present invention, and any one of various corn syrups commercially available may be utilized.

The compressible sucrose composition also serves both as a sweetener and a binding agent. It is preferably of the type commercially-available and known as Di-Pac. While it is not necessary to include both a compressible sucrose composition and a corn syrup solids composition, as indicated in Table 1, it was found that wafers incorporating only compressible sucrose as its binding agent exhibited an undesirably great degree of friability tending to crumble much too readily to retain the appearance and feel of a cookie or biscuit. Wafers incorporating only corn syrup solids as their binding agent were found to exhibit an undesirably low degree of friability, appearing to be much too hard to be comfortably chewed by young children. A mixture, however, in substantially equal amounts of the two compositions proved to exhibit a desirable level of both friability and taste. The resulting wafers incorporating substantially equal amounts of compressible sucrose and corn syrup solids compositions exhibited the richness in flavor characteristic of the compressible sucrose coupled with enough wafer cohesiveness to prevent premature crumbling at the wafer edges.

The remaining compositions in Table 1, namely the chocolate cream flavor, the vanilla dry flavor, and the additive sweetener, are commercially available flavor enhancers included to optimize the taste emulation of popular cookie products. Although the chocolate cream flavor, the vanilla dry flavor, and the additive sweetener are not therapeutically active, they do provide an important function of the overall antidotal food product in that their combined presence optimizes the probability that the young child will ingest the antidotal food product in emergency conditions and thereby allow the therapeutically active ingredients to take effect. Thus, such ingredients are important in the overall concept since they render the therapeutically active ingredients functional in a particular environment. Other suitable flavoring composition may be incorporated to serve this purpose; however, it is important to maintain the proportional quantities of such flavor enhancers at the low levels indicated in Table 1 to prevent the occurrence of unexpected levels of adsorptivity interference with respect to the activated charcoal. Accordingly, care must be taken not to introduce into the wafer in any amount a flavoring composition which, by its inherent properties, exhibits an inordinate tendency to interfere with activated charcoal adsorptivity. It was found in an early prototype of the subject wafer, for instance, that the incorporation of melted chocolate as a flavor enhancer caused a noticeable decrease in the activated charcoal's adsorptivity. This was likely due to the inherent tendency of the melted chocolate to adhere to the charcoal particles and plug their pores to thereby measurably reduce the available adsorption surface area.

Regarding the component compositions of the filling composition shown in Table 2, such is important in that they combine in the indicated proportions to form a sweet, creamy filling which complements the dry, somewhat diluted sweetness of the wafers, tending thereby to prompt the user to chew the wafers over a longer period of time. This increased chewing time is important, for the more the wafer is chewed, the more the activated charcoal is dispersed. Kinetics tests performed with various wafer prototypes, as discussed in following paragraphs, indicate that greater dispersement of the activated charcoal effects measurably faster rates of toxin adsorption.

Observations from numerous other tests indicate that the component compositions of the filling present no significant threat to adsorptivity of the activated charcoal contained in the wafers. Accordingly, the choice of component compositions and their respective weight percentages are important to the present invention to the extent that they affect the consistency, color, and taste of the resulting filling. The particular choice of component compositions and their corresponding weight percentages are determined primarily by these considerations. The component compositions shown in Table 2 are each devoid of a fat component, a feature desirable in light of interference tests. Interference tests for various component compositions indicate that fat-containing compositions observably interfere with the activated charcoal contained in the wafers.

Referring now to the tests performed for the subject decontaminant food product, extensive tests were performed on each of the more than forty prototypes developed in the process of realizing a workable decontaminant food product that overcomes the shortcomings of the prior art. Comparative kinetics tests to determine the rate at which a given prototype adsorbed a. toxin, equilibrium adsorption tests to determine the adsorption capacity of the given prototype, and, where necessary, interference tests to determine the degree by which isolated component compositions tend to diminish the adsorptivity of the activated charcoal in the given prototype were performed for each prototype under simulated conditions. The tested prototypes varied widely in their component compositions and the corresponding proportional quantities, and the most instructive of the test results obtained are discussed in following paragraphs.

All tests were conducted in vitro by mixing a predetermined amount of a test substance into a stock solution. The in vitro stock solution used in each test consisted of 1 g/L of sodium salicylate dissolved in a simulated gastric fluid solution containing 2.0 g/L of NaCl, 7.0 mL/L of 12 N strength concentrated HCl, and distilled water. The simulated gastric fluid was characterized in this form by a pH level of 1.2, the salicylate at this pH level being more than 99.99% in the form of undissociated salicylic acid, which is very similar in its properties to aspirin, or acetylsalicylic acid.

Equilibrium adsorption tests for determining the total amount of salicylate that a given test substance may potentially adsorb if allowed to attain equilibrium conditions was conducted with the following procedures. First, a predetermined amount of the substance to be tested was placed in a glass vial, and 20 mL of the stock solution was added to that vial. The vial was thereafter continuously shaken by placement on a shaking table for approximately 15 hours. This caused the test substance to fully disintegrate such that the activated charcoal contained therein attained virtually perfect adsorption equilibrium with the salicylate in the stock solution.

The kinetics tests were conducted generally by performing the following steps. Approximately 500 mL of the stock solution was poured into a one liter glass container. A predetermined quantity of the given test substance was then introduced into the solution in the glass container. The container was then placed on a shaking table and shaken thereby at a 60 cycles per minute oscillation frequency. Samples were taken at various times. Activated charcoal was filtered from each sample and the solution analyzed colorimetrically to determine the salicylate concentration corresponding to the given sample time.

Comparative kinetics test results for a cookie product formed by sandwiching a pair of wafers formulated in accordance with the preferred combination indicated in Table 1 sandwiched about a filling formulated in accordance with Table 2 are shown in FIG. 1. For this test, a cookie weighing 6.80 g (5.15 g wafers and 1.65 g filling) was chewed vigorously by the individual conducting the test, then introduced into a given volume of the stock solution. At 40% of the wafer weight, approximately 2.06 g of A Supra activated charcoal was thereby introduced into the solution. As shown by curve 10, the concentration of salicylate in the solution decreased from 1.0 g/L to under 0.2 g/L within 2.5 minutes after the cookie's introduction into the solution. After this dramatic initial decrease, the rate of salicylate concentration decrease gradually declined until equilibrium conditions were reached (not shown).

The superior adsorption performance of the subject decontaminant food product is apparent when curve 10 is compared with curve 20 plotting the decrease in salicylate concentration upon introduction therein of a commonly available prior art activated charcoal liquid suspension. Curve 20 was obtained by introducing 11 g of ACTIDOSE AQUA, a liquid suspension commercially marketed by Paddock Labs, Inc., Minneapolis, MN. That amount of ACTIDOSE AQUA was determined to contain approximately the equivalent amount of activated charcoal as contained in the cookie sample from which curve 10 was derived. Comparison of the two curves indicates that the cookie formed in accordance with the present invention not only reduced the salicylate concentration in the simulated gastric fluid solution at a significantly faster rate, but also yielded a significantly greater overall reduction in that concentration than a comparable amount of ACTIDOSE AQUA suspension. At the five minute point, for instance, the salicylate concentration, upon introduction of the subject cookie, was slightly below 0.1 g/L, whereas the salicylate concentration upon introduction of ACTIDOSE AQUA into the solution was observed to be slightly below 0.5 g/L at that time. After 30 minutes, the salicylate concentration had diminished to approximately 0.03 g/L with the subject cookie, whereas it had begun to level off at approximately 0.15 g/L with ACTIDOSE AQUA.

The degree of interference with the adsorptivity of the activated charcoal in the cookie sample corresponding to curve 10 may be determined by comparison with the adsorption performance of an appropriate quantity of the same activated charcoal alone. That adsorption performance is indicated by curve 30, derived by introducing into the stock solution approximately 2.0 g of pure A Supra activated charcoal powder. Comparison of curves 10 and 30 does indicate a measure of interference with the charcoal's adsorptivity; and, while the resolution of the curves in FIG. 1 is not sufficient to quantifiably represent that measure of interference, separately conducted equilibrium adsorption tests show that the interference is not at a significant level. Those equilibrium adsorption tests conducted with pure A Supra activated charcoal yielded an approximate 75% adsorption compared to the 68.5% adsorption obtained with a sample of the subject cookie. That equates to a reduction of approximately 6.5% in the resulting adsorption of salicylate. In light of the vital benefits derived from the enticing flavor and friability of the subject decontaminant food product, the cost in adsorptivity would be found by most toxicological treatment professionals to be quite insignificant.

The pleasant flavor introduced into each wafer by the additional component compositions not only encourage thorough and complete chewing which enhances the adsorption kinetics by dispersing the activated charcoal contained in the wafer, it also has a more direct effect on the charcoal dispersion. The pleasant flavor induces the user's salivary glands to produce more saliva than it would otherwise produce in the absence of such a pleasant flavor. The additional saliva, in turn, serves as a vehicle for more efficient dispersion of the charcoal particles.

Referring now back to Table 1, it is preferable that A Supra activated charcoal be incorporated into each wafer at a 40% weight percentage. A reduction in the weight percentage of A Supra activated charcoal leads to a corresponding reduction in the adsorptivity of the resulting cookie. This was borne out in equilibrium adsorption tests conducted with a 30 weight percent A Supra powdered wafer wherein adsorption values in the range of 61.1% to 64.9% were observed. In tests with a 20 weight percent A Supra powdered wafer sample, the range of adsorption values observed decreased to 44.9% to 46.3%.

An increase in the weight percentage of A Supra beyond 40%, while possible without excessively detrimental effects on the resulting wafer's flavor and friability, would nevertheless tend to reduce the wafer's palatability to younger children who are more inclined than older consumers to reject a food product for lack of sweetness.

Other than the activated charcoal component, the other primary components of each wafer, the corn syrup solids (CSS) and the DiPac compositions may be varied in their proportional quantities. Those two compositions combine to form the main components of the flavored binding composition, and variations in their relative proportional quantities in that binding composition notably affect the flavor and friability of the resulting wafer. As shown in Table 3, the relative proportions of the CSS and DiPac compositions, however, do not appear to affect the adsorptivity of the activated charcoal.

TABLE 3

| RELATIVE PROPORTIONS | PERCENT SALICYLATE ADSORBED |
|---|---|
| 100% CSS, 0% DiPac | 68.49% |
| 75% CSS, 25% DiPac | 68.49% |
| 50% CSS 50% DiPac, | 68.22% |
| 0% CSS, 100% DiPac | 68.49% |

Comparative evaluation of the wafers resulting from each binding composition formulation shown in Table 3 indicates that the corn syrup solids component is a stronger binding agent than the DiPac component. Accordingly, a wafer incorporating the 100% CSS—0% DiPac formulation was more resistant to finger-abrasion than was a wafer incorporating the 75% CSS—25% DiPac formulation, which, in turn, was more resistant to finger abrasion than a wafer incorporating the 50% CSS—50% DiPac formulation, or one incorporating the 0% CSS—100% DiPac formulation. The resistance to abrasion of wafers incorporating the 50% CSS—50% DiPac and the 0% CSS—100% DiPac formulations were qualitatively, at least, indistinguishable.

Comparative flavor evaluation of wafers incorporating the formulations shown in Table 3 indicates that a wafer incorporating the 100% CSS—0% DiPac formulation had little, if any, sweet flavor. A wafer incorporating the 75% CSS—25% DiPac formulation had a mildly sweet, subtle chocolate flavor. A wafer incorporating the 50% CSS—50% DiPac formulation had a more defined sweet chocolate flavor, and a wafer incorporating 0% CSS—100% DiPac had an even more distinct sweet chocolate flavor. It is thus preferable for the optimal combination of friability level and flavor to incorporate into each wafer a 50% corn syrup solids—50% DiPac binding composition formulation.

The filling composition formulated in accordance with Table 2 offers a concentrated sugary flavor which supplements and augments the flavor of the wafers. Often, however, consumed cookie sandwich treats are consumed in parts by children who first disassemble the sandwich by separating at least one wafer from the filling, then proceed to consume the separated parts in sequence rather than in toto. It is, therefore, preferable that the wafers in and of themselves exhibit substantial flavor to be desirable to the average young child's palate separate and apart from any filling composition.

The combination of component compositions shown in Table 1 for each wafer of the subject decontaminant food product was obtained only after extensive testing of numerous formulations incorporating a wide variety of component compositions and in varying proportional quantities. One flavored binding agent considered in place of the corn syrup solids and DiPac compositions was a composition commercially marketed as Maltrin 700, a tabletting agent. Adsorbance tests conducted by combining the Maltrin 700 with a sample of A Supra activated charcoal, however, indicated that the Maltrin 700 significantly interferes with the adsorptivity of the activated charcoal. In those tests, 0.0203 g of A Supra activated charcoal was combined with 0.0779 g of Maltrin 700 and introduced into a predetermined volume of the stock solution. A separate 0.0203 g sample of A Supra activated charcoal was introduced into a second separate sample of the same stock solution. In a third separate sample of the stock solution, 0.0203 g of A Supra activated charcoal and 0.0779 g of Maltrin 700 combined and compressed into a tableted wafer form was introduced after the wafer had been sufficiently crushed. The comparative adsorption results obtained are shown in Table 4.

TABLE 4

| TEST SUBSTANCE | PERCENT SALICYLATE ADSORBED | RELATIVE PERFORMANCE |
| --- | --- | --- |
| Pure A Supra Activated Charcoal | 58.24% | 100.0% |
| A Supra Activated Charcoal and Maltrin 700 | 51.92% | 89.1% |
| A Supra Activated Charcoal and Maltrin 700 in Tableted Wafer Form | 40.50% | 69.5% |

As the results in Table 4 show, Maltrin 700, when simply blended with A Supra powder interfered with the activated charcoal's adsorptivity by approximately 11%. More importantly, the Maltrin 700, when thoroughly blended and tightly compressed with the A Supra activated charcoal powder as it would be in the tableted wafer form of the subject decontaminant food product, interfered by more than an alarming 30%. Maltrin 700 was eliminated as a preferable component composition on this basis, as were numerous other possible compositions.

Among the many prototype wafer formulations tested was that for which the component compositions and their proportional quantities are shown in Table 5. Equilibrium adsorption tests conducted for this prototype wafer formulation yielded adsorptivity measures that were significantly less than expected. Interference tests were conducted for each of the components outside of activated charcoal to isolate the cause of the reduced adsorptivity. Those tests indicated that the reduction in adsorptivity was due primarily to the inordinate levels of interference attributable to the melted chocolate and the emulsifier composition used in the formulation commercially marketed as Dur-Lo.

Figure 2:
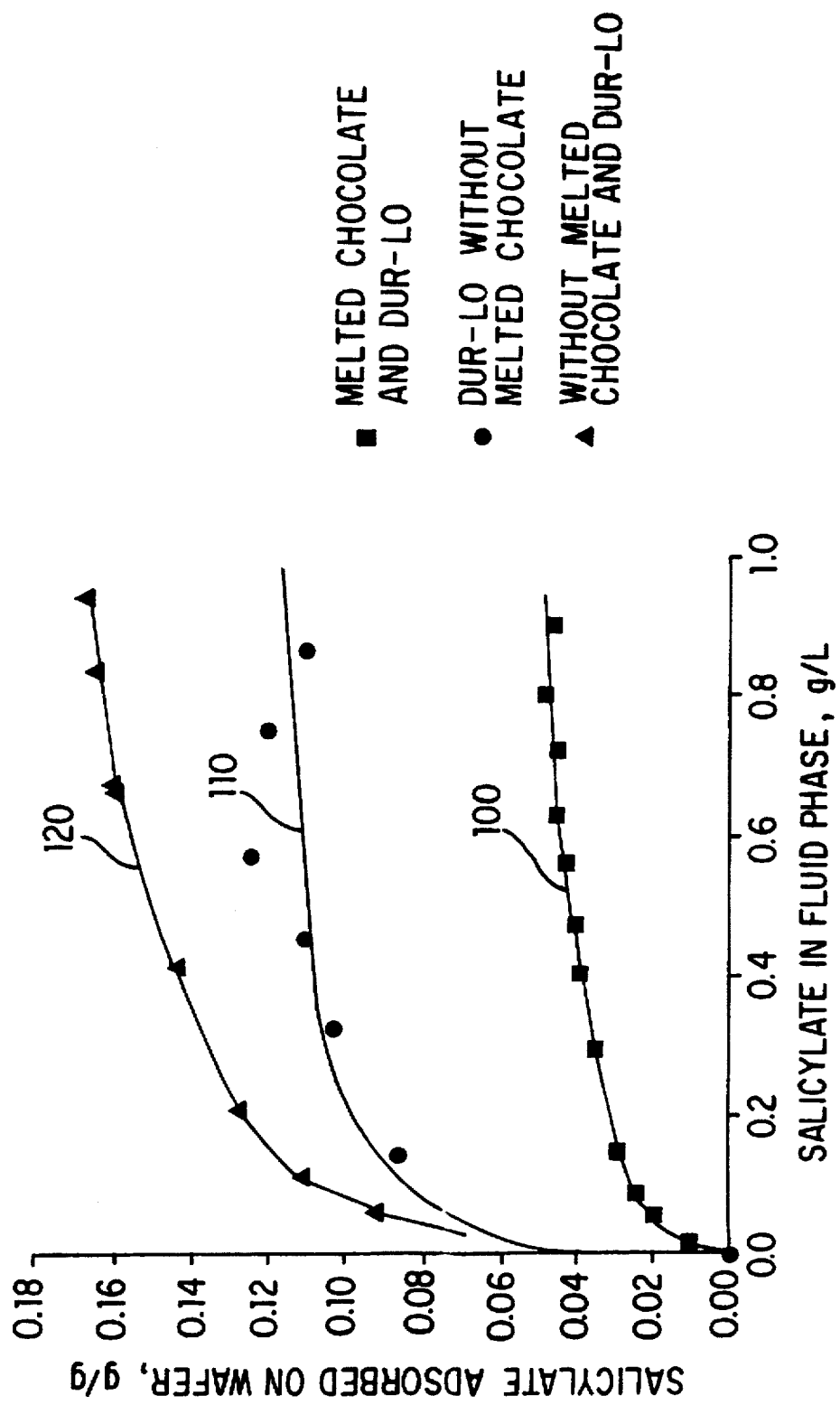
FIG. 2 is a graphical representation of equilibrium adsorption test data illustrating the interfering effects of a composition tested during development of the preferred embodiment of the subject decontaminant food product; and, FIG. 3 is a block diagram illustrating the sequence of steps in the preferred method of forming the preferred embodiment of the subject decontaminant food product.

For comparison purposes, prototype wafers were formulated, as shown respectively in Tables 6 and 7, first without the melted chocolate composition, then without either of the melted chocolate and the Dur-Lo emulsifier compositions. Equilibrium adsorption tests were then performed for each prototype formulation. The isotherms for these prototype wafer formulations (of Table 5, Table 6, and Table 7) are shown in FIG. 2 as curves 100, 110, and 120, respectively. The melted chocolate component in Table 5 was replaced for the Table 6 and 7 prototypes with a cocoa powder composition, as a chocolate flavor is a desirable characteristic of the resulting wafer, regardless of the formulation used.

TABLE 5

| COMPONENT COMPOSITION | QUANTITY (g) |
| --- | --- |
| Granulated Sugar | 0.550 |
| Non-Fat Dry Milk | 0.175 |
| Salt | 0.050 |
| Baking Soda | 0.075 |
| Monocalcium Phosphate | 0.025 |
| Vanilla Flavor | 0.100 |
| Sorbitol Liquid | 2.600 |
| Glycerine | 1.300 |
| Melted Chocolate | 0.700 |
| Cake Flour | 1.300 |
| Dur-Lo Emulsifier | 0.400 |
| A Supra Activated Charcoal | 2.025 |

TABLE 6

| COMPONENT COMPOSITION | QUANTITY (g) |
| --- | --- |
| Granulated Sugar | 0.550 |
| Non-Fat Dry Milk | 0.175 |
| Salt | 0.050 |
| Baking Soda | 0.075 |
| Monocalcium Phosphate | 0.025 |
| Vanilla Flavor | 0.100 |
| Sorbitol Liquid | 2.600 |
| Glycerine | 1.300 |
| Brown Cocoa Powder | 1.400 |
| Cake Flour | 1.300 |
| Dur-Lo Emulsifier | 0.400 |
| A Supra Activated Charcoal | 2.025 |

TABLE 7

| COMPONENT COMPOSITION | QUANTITY (g) |
| --- | --- |
| Granulated Sugar | 0.550 |
| Non-Fat Dry Milk | 0.175 |
| Salt | 0.050 |
| Baking Soda | 0.075 |
| Monocalcium Phosphate | 0.025 |
| Vanilla Flavor | 0.100 |
| Sorbitol Liquid | 2.600 |
| Glycerine | 1.300 |
| Brown Cocoa Powder | 1.400 |
| Cake Flour | 1.300 |
| A Supra Activated Charcoal | 2.025 |

Referring to FIG. 2, isotherm 110 (corresponding to Table 6) clearly shows that the absence of melted chocolate but with the use of Dur-Lo affords a significant increase in the adsorptivity observed when taken with respect to isotherm 100 (corresponding to Table 5). Isotherm 120 without Dur-Lo and melted chocolate shows, further, that the absence of both melted chocolate and the Dur-Lo emulsifier in the tested wafer affords an even greater increase in the observed adsorptivity over that of isotherm 100. It is not readily apparent why this marked increase in interference is attributable to the melted chocolate and Dur-Lo emulsifier compositions in such an inordinate measure relative to the levels of interference attributable to the other component compositions. Whatever the specific cause, it is likely that the unique physical properties of the melted chocolate and Dur-Lo components in some measure cause them to bind with the activated charcoal particles, filling many of the pores that otherwise would give each activated charcoal particle a greater internal surface area. The adsorptivity of the given activated charcoal particle is thus severely curtailed.

Figure 3:
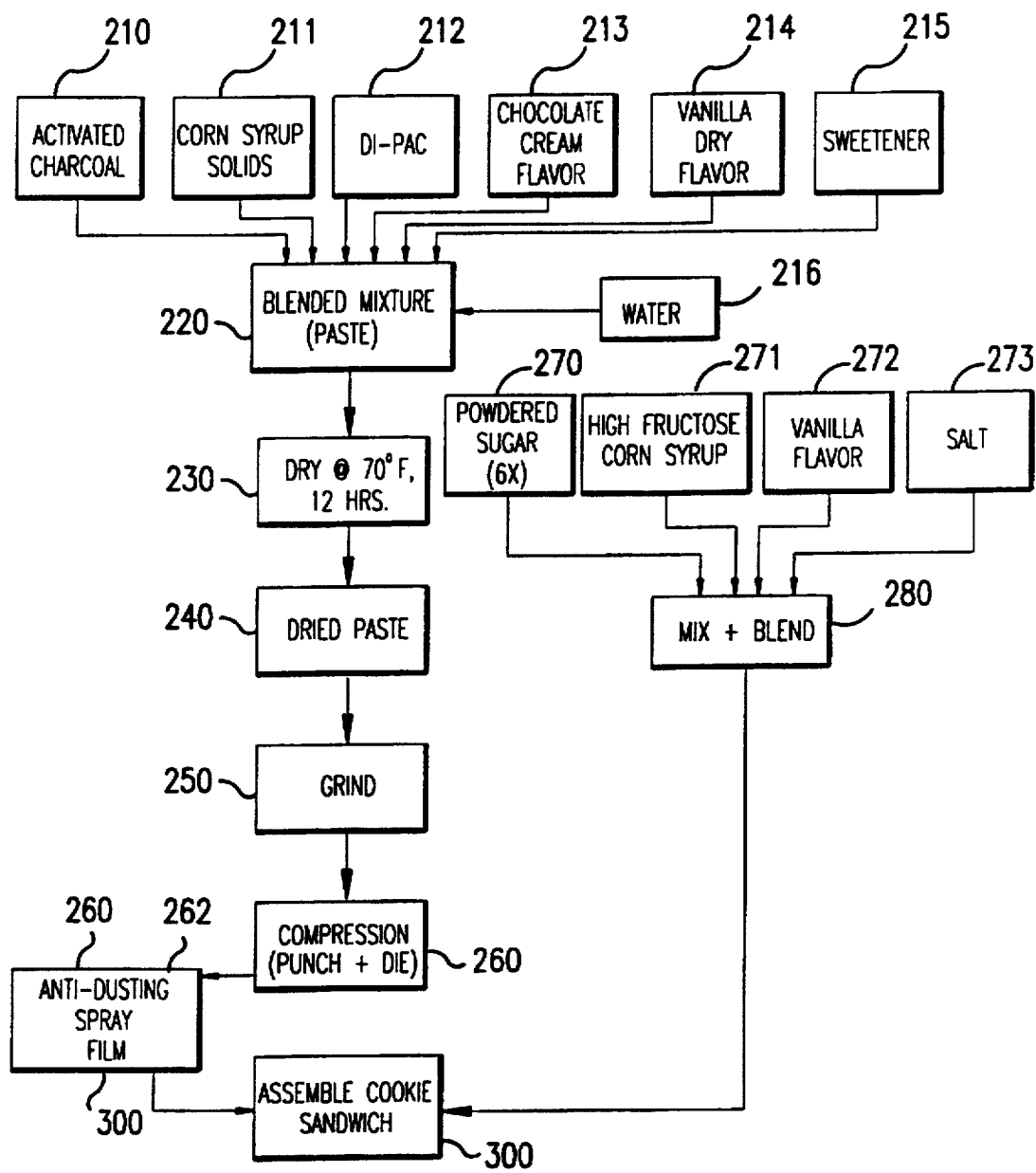

Referring now to FIG. 3, there is shown a preferred method for forming the decontaminant food product of the present invention, in its preferred cookie sandwich form. Appropriate quantities of the base wafer ingredients in the approximate weight percentage ranges of Table 1: activated charcoal 210, corn syrup solids 211, Di-Pac 212, chocolate cream flavor 213, vanilla dry flavor 214, and sweetener 215, are evenly blended at step 220 into a paste. As necessary, a limited quantity of water 216 is mixed into the paste to facilitate the malleability of the paste and thereby enhance the homogeneity obtained in the blend. After sufficient blending, the paste is allowed to dry at step 230, at room temperature approximating 70° F., for approximately 12 hours resulting in a dry paste composition. The dried paste 240 is then ground at step 250 in a Wiley mill, employing preferably a 20 or 40 mesh screen. The ground preparation is then compressed at step 260 in, preferably, a one inch punch and die assembly set to impart at least 15,000 psi compression pressure when a 1.0" diameter wafer is compressed and may be set at 40,000 psi compression pressure when a larger wafer in the order of 1.75" diameter is used. A plurality of wafers are formed by the aforementioned steps.

The wafer may then be sprayed with an anti-dusting spray film in step 262 in order to cover the activated charcoal particulates in order to minimize the smearing of the activated charcoal when being grasped by a user. The spray film is a sugar film formed of sucrose or dextrose or some like composition to form an encapsulation.

The filling is then prepared by mixing and evenly blending at step 280 appropriate quantities of powdered sugar 270, preferably having a 6X granularity, high fructose corn syrup 271, vanilla flavor 272, and salt 273. An appropriate quantity of the resulting creamy mixture is then placed between a pair of wafers to assemble at step 300 a cookie sandwich decontaminant food product.

Although this invention has been described in connection with specific forms and embodiment thereof, it will be appreciated that various modifications other than those discussed above may be resorted to without departing from the spirit or scope of the invention. For example, functionally equivalent elements may be substituted for those specifically shown and described, proportional quantities of the elements shown and described may be varied, and in the formation method steps described, particular steps may be reversed or interposed, all without departing from the spirit or scope of the invention as defined in the appended Claims.

What is claimed is:

1. A toxin decontaminant food product for ingestion into the gastro-intestinal tract of a user comprising:
   a substantially dry friable wafer adapted to be chewed by a user for ingestion into said gastro-intestinal tract of the user, said dry friable wafer including a wafer mixture composition formed by blending a first predetermined weight of a sorbent particulate composition having an initial adsorption value with respect to a toxin with a second predetermined weight of a substantially non-interfering flavored binding composition to form said wafer with a consistency emulating that of a baked cookie, said initial adsorption value of said sorbent particulate composition being substantially maintained in said wafer mixture composition.

2. The toxin decontaminant food product as recited in claim 1 wherein said sorbent composition includes activated charcoal.

3. The toxin decontaminant food product as recited in claim 2 wherein said activated charcoal is characterized by an approximate internal surface area of 2,000 m²/g.

4. The toxin decontaminant food product as recited in claim 3 wherein said dry friable wafer includes said activated charcoal in the approximating weight range of 20.0% to 60.0% thereof.

5. The toxin decontaminant food product as recited in claim 4 wherein said dry friable wafer includes a corn syrup solids composition in the approximating weight range of 0% to 78.0% thereof.

6. The toxin decontaminant food product as recited in claim 5 wherein said dry friable wafer includes a compressible sucrose composition in the approximating weight range of 0% to 78.0% thereof.

7. The toxin decontaminant food product as recited in claim 6 wherein said dry friable wafer includes a chocolate cream flavor composition in the approximating weight range of 0.5% to 2.0% thereof.

8. The toxin decontaminant food product as recited in claim 7 wherein said dry friable wafer includes a particulate vanilla flavor composition in the approximating weight range of 0.5% to 2.0% thereof.

9. The toxin decontaminant food product as recited in claim 8 wherein said dry friable wafer includes a sweetener additive composition in the approximating weight range of 0.1% to 1.0% thereof.

10. The toxin decontaminant food product as recited in claim 9 including at least a pair of said dry friable wafers and a flavored filling portion sandwiched therebetween, said filling portion being characterized by a creamy consistency.

11. The toxin decontaminant food product as recited in claim 10 wherein said filling portion includes:
    (a) a powdered sugar composition in the approximate weight percentage of 76.34% of said filling portion;
    (b) a high fructose corn syrup composition in the approximate weight percentage of 22.90% of said filling portion;
    (c) a vanilla flavor composition in the approximate weight percentage of 0.63% of said filling portion; and,
    (d) a salt composition in the approximate weight percentage of 0.13% of said filling portion.

12. A toxin decontaminant cookie product for ingestion into the gastro-intestinal tract of a user comprising:
    (a) at least a pair of substantially dry friable wafers adapted to be chewed by a user for ingestion into said gastro-intestinal tract of the user, each said dry friable wafer including a wafer mixture composition formed by blending a first predetermined weight of a sorbent particulate composition having an initial adsorption value with respect to a toxin with a second predetermined weight of a substantially non-interfering flavored binding composition, said initial adsorption value of said sorbent particulate composition being substantially maintained in said wafer mixture composition; and,
    (b) a flavored filling portion sandwiched between said dry friable wafers for augmenting and supplementing the flavor of said dry friable wafers, said filling portion having a creamy consistency.

13. The toxin decontaminant cookie product as recited in claim 12 wherein said sorbent composition includes activated charcoal.

14. The toxin decontaminant cookie product as recited in claim 13 wherein said activated charcoal is characterized by an approximate internal surface area of 2,000 m²/g.

15. The toxin decontaminant cookie product as recited in claim 14 wherein each said dry friable wafer includes said activated charcoal in the approximating weight range of 20.0% to 60.0% thereof.

16. The toxin decontaminant cookie product as recited in claim 15 wherein each said dry friable wafer includes a corn syrup solids composition in the approximating weight range of 0% to 78.0% thereof.

17. The toxin decontaminant cookie product as recited in claim 16 wherein each said dry friable wafer includes a compressible sucrose composition in the approximating weight range of 0% to 78.0% thereof.

18. The toxin decontaminant cookie product as recited in claim 17 wherein each said dry friable wafer includes a chocolate cream flavor composition in the approximating weight range of 0.5% to 2.0% thereof.

19. The toxin decontaminant cookie product as recited in claim 18 wherein each said dry friable wafer includes a particulate vanilla flavor composition in the approximating weight range of 0.5% to 2.0% thereof.

20. The toxin decontaminant cookie product as recited in claim 19 wherein each said dry friable wafer includes a sweetener additive composition in the approximating weight range of 0.1% to 1.0% thereof.

21. The toxin decontaminant cookie product as recited in claim 20 wherein said filling portion includes:

(a) a powdered sugar composition in the approximate weight percentage of 76.34% of said filling portion;

(b) a high fructose corn syrup composition in the approximate weight percentage of 22.90% of said filling portion;

(c) a vanilla flavor composition in the approximate weight percentage of 0.63% of said filling portion; and, (d) a salt composition in the approximate weight percentage of 0.13% of said filling portion.

22. A method of forming a toxin decontaminant food product for ingestion into the gastro-intestinal tract of a user comprising the steps of:

(a) blending a first predetermined weight of a sorbent particulate composition having an initial adsorption value with respect to a toxin with a second predetermined weight of a substantially non-interfering flavored binding composition to form a paste mixture composition, said initial adsorption value of said sorbent particulate composition being substantially maintained in said paste mixture composition;

(b) heating said paste mixture composition for a predetermined drying time at a predetermined drying temperature to form a dried mixture composition;

(c) grinding said dried mixture composition to form a pulverized mixture composition; and, (d) compressing said pulverized mixture composition at an approximate compression pressure of at least 15,000 psi to form a dry friable wafer.

23. The method for forming a toxin decontaminant food product as recited in claim 22 wherein said sorbent particulate composition includes activated charcoal.

24. The method for forming a toxin decontaminant food product as recited in claim 23 wherein said activated charcoal is characterized by an approximate internal surface area of 2,000 m²/g.

25. The method for forming a toxin decontaminant food product as recited in claim 24 wherein said paste mixture composition includes said activated charcoal in the approximating weight range of 20.0% to 60.0% thereof.

26. The method of forming a toxin decontaminant food product as recited in claim 25 wherein said flavored binding composition includes a corn syrup solids composition in the approximating weight range of 0% to 78.0% of said paste mixture composition.

27. The method of forming a toxin decontaminant food product as recited in claim 26 wherein said flavored binding composition includes a compressible sucrose composition in the approximating weight range of 0% to 78.0% of said paste mixture composition.

28. The method of forming a toxin decontaminant food product as recited in claim 27 wherein said flavored binding composition includes a chocolate cream flavor composition in the approximating weight range of 0.5% to 2.0% of said paste mixture composition.

29. The method of forming a toxin decontaminant food product as recited in claim 28 wherein said flavored binding composition includes a particulate vanilla flavor composition in the approximating weight range of 0.5% to 2.0% of said paste mixture composition.

30. The method for forming a toxin decontaminant food product as recited in claim 29 wherein said flavored binding composition includes a sweetener additive composition in the approximating weight range of 0.1% to 1.0% of said paste mixture composition.

31. The method for forming a toxin decontaminant food product as recited in claim 30 wherein said predetermined drying temperature is 140° Fahrenheit.

32. The method for forming a toxin decontaminant food product as recited in claim 31 wherein said predetermined drying time is 12 hours.

33. The method for forming a toxin decontaminant food product as recited in claim 30 further including the steps of:

(a) forming at least a pair of said dry friable wafers;

(b) blending together predetermined weights of a powdered sugar composition, a high fructose corn syrup composition, a vanilla flavor composition, and a salt composition to form a filling mixture composition; and, (c) sandwiching said filling mixture composition between said dry friable wafers.

34. The method of forming a toxin decontaminant food product as recited in claim 31 wherein said filling mixture composition includes:

(a) said powdered sugar composition in the approximate weight percentage of 76.34% of said filling mixture composition;

(b) said high fructose corn syrup composition in the approximate weight percentage of 22.90% of said filling mixture composition;

(c) said vanilla flavor composition in the approximate weight percentage of 0.63% of said filling mixture composition; and, (d) said salt composition in the approximate weight percentage of 0.13% of said filling mixture composition.

35. The toxin decontaminant food product as recited in claim 1 where said binding composition includes a corn syrup solids composition and a compressible sucrose composition.

36. The toxin decontaminant food product as recited in claim 35 where said corn syrup solids composition and said compressible sucrose composition are combined in substantially equal weight percent proportions.

37. The toxin decontaminant food product as recited in claim 35 where said corn syrup solids composition and said compressible sucrose composition are each included in an amount approximating 28.8 weight percent.

38. The toxin decontaminant food product as recited in claim 1 where said sorbent particulate composition includes activated charcoal in an amount approximating 40.0 weight percent.

* * * * *